(12) United States Patent
Van Reen et al.

(10) Patent No.: US 10,850,061 B2
(45) Date of Patent: Dec. 1, 2020

(54) LIGHTING SYSTEM FOR CIRCADIAN CONTROL AND ENHANCED PERFORMANCE

(71) Applicant: BROWN UNIVERSITY, Providence, RI (US)

(72) Inventors: Eliza Van Reen, East Greenwich, RI (US); Gustavo E. Fernandes, Providence, RI (US); Jingming Xu, Providence, RI (US); Mary A. Carskadon, Providence, RI (US)

(73) Assignee: Brown University, Providence, RI (US)

( * ) Notice: Subject to any disclaimer, the term of this patent is extended or adjusted under 35 U.S.C. 154(b) by 152 days.

(21) Appl. No.: 15/991,681

(22) Filed: May 29, 2018

(65) Prior Publication Data
US 2018/0339127 A1  Nov. 29, 2018

Related U.S. Application Data

(60) Provisional application No. 62/654,790, filed on Apr. 9, 2018, provisional application No. 62/511,692, filed on May 26, 2017.

(51) Int. Cl.
*A61M 21/02* (2006.01)
*A61N 5/06* (2006.01)
*A61M 21/00* (2006.01)

(52) U.S. Cl.
CPC .......... *A61M 21/02* (2013.01); *A61N 5/0618* (2013.01); *A61M 2021/0044* (2013.01);
(Continued)

(58) Field of Classification Search
CPC .............. A61M 21/02; A61M 21/0094; A61M 2021/005; A61M 2205/59
(Continued)

(56) References Cited

U.S. PATENT DOCUMENTS

| | | | | |
|---|---|---|---|---|
| 6,053,936 A | * | 4/2000 | Koyama | A61M 21/00 600/27 |
| 6,623,512 B1 | * | 9/2003 | Heller | A61M 21/00 128/898 |

(Continued)

FOREIGN PATENT DOCUMENTS

WO    2016180235 A1    11/2016

OTHER PUBLICATIONS

Gall, D et al. Definition and measurement of circadian radiometric quantities. Light and health—non-visual effects : proceedings of the CIE symposium '04: Sep. 30-Oct. 2, 2004, Vienna, Austria.—Wien: Commission internationale de l'éclairage, 2004, S. 29-32 (2004).

(Continued)

*Primary Examiner* — Samuel G Gilbert
(74) *Attorney, Agent, or Firm* — Adler Pollack & Sheehan P.C.

(57) ABSTRACT

Systems tune, control, or remediate the intrinsic Circadian clock. A light controller sets spectral distribution, intensity of a bioactive spectral band to shift or entrain circadian response to enhance performance and/or synchronize with local or expected conditions. The systems enhance performance under conditions that might be changing, disrupted, or otherwise present an irregular phase or unnatural change in the subject's circadian status, for example, due to geographically discontinuous activity or spectrally deficient (Continued)

workplace illumination, or due to divergent individual sleep/wake behaviors of subjects in a structured group activity. An illumination recipe that compensates for the deficiency of lighting or of participant sleep or behavior patterns, or age- or disease-related changes, to evoke, shift, or align circadian response and improve behaviors such as classroom alertness, relaxation, excitability, attention, or focus. Systems may receive sensed light values and automatically apply high- and/or low-CER illumination to effect the intended circadian phase.

24 Claims, 16 Drawing Sheets

(52) U.S. Cl.
CPC ............. *A61M 2205/3306* (2013.01); *A61M 2205/3553* (2013.01); *A61M 2205/3569* (2013.01); *A61M 2205/3592* (2013.01); *A61M 2230/06* (2013.01); *A61M 2230/50* (2013.01); *A61M 2230/63* (2013.01); *A61N 2005/0627* (2013.01); *A61N 2005/0628* (2013.01)

(58) Field of Classification Search
USPC .................................................. 600/26–28
See application file for complete search history.

(56) References Cited

U.S. PATENT DOCUMENTS

| | | |
|---|---|---|
| 2006/0165786 A1 | 7/2006 | Lewy et al. |
| 2007/0045049 A1* | 3/2007 | Nien ................ E06B 7/086 186/52 |
| 2010/0076250 A1* | 3/2010 | Van Woudenberg ................ A61M 21/00 600/27 |
| 2016/0158486 A1 | 6/2016 | Colbaugh et al. |

OTHER PUBLICATIONS

Khalsa, SBS et al. A phase response curve to single bright light pulses in human subjects. Journal of Physiology—London, vol. 549, pp. 945-952 (2003).

Oh, JH et al. Healthy, natural, efficient and tunable lighting: four-package white LEDs for optimizing the circadian effect, color quality and vision performance. Light Sci. Appl. 3, e141 (2014).

Ruger, M et al. Human phase response curve to a single 6.5 h pulse of short-wavelength light. JJournal of Physiology—London, vol. 591, pp. 353-363 (2013).

Zeitzer, DJ et al. Sensitivity of the human circadian pacemaker to nocturnal light: melatonin phase resetting and suppression. Journal of Physiology—London, vol. 526, pp. 695-702 (2000).

International Search Report and Written Opinion of the International Search Authority in PCT/US18/34889 dated Aug. 23, 2018 (9 pgs.).

* cited by examiner

FIG. 8A
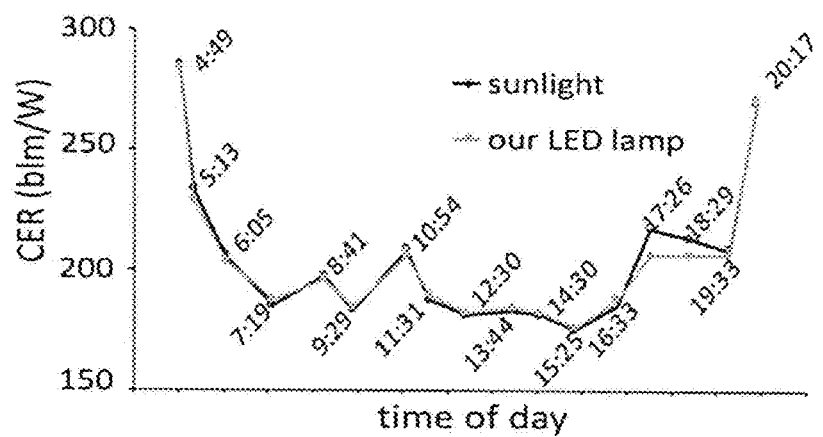
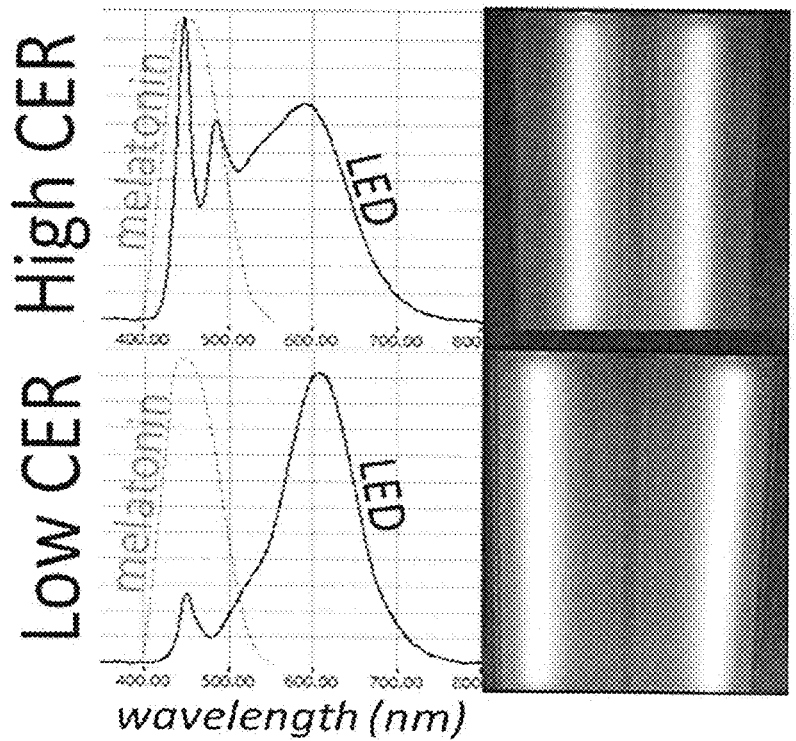
FIG. 8B

LIGHTING SYSTEM FOR CIRCADIAN CONTROL AND ENHANCED PERFORMANCE

GOVERNMENT SUPPORT

This invention was made with government support under grant numbers 1430007 awarded by the National Science Foundation. The government has certain rights in the invention

BACKGROUND AND TECHNICAL FIELD

This invention relates to workplace lighting and to enhancing focus, attention, sleep, mood and restfulness; it also relates to mitigating effects of schedule changes, travel and organization or tasks.

The economic burden of sleep loss has been estimated at $411 billion per year in the United States. Sleep and circadian rhythms influence human performance, impulsivity, decision-making, learning, memory, attention, alertness, and overall physical and mental health. The demand for humans to perform critical work-related tasks at adverse circadian phases (i.e., biological night) while lacking adequate sleep has played a role in some of the world's most devastating industrial and engineering disasters (such as Chernobyl, Three Mile Island, the Challenger explosion, Exxon Valdez, American Airlines Flight 1420, etc.). Where performance, alertness, and attention are critical for success military, professional sports, medical/health care, transportation, school/training etc. or other organizations operating with defined or changing schedules, may be impacted by effects on personnel of interactions between inadequate sleep and adverse circadian phase. Current knowledge of how sleep and circadian rhythms are regulated have allowed for experimental manipulation of sleep and circadian factors in order to improve performance outcomes. There also exist many specific or institutional situations in which individuals live or work in an artificial or institutional milieu, in which the lighting conditions, sleep/wake schedules, the activities of the occupants, and their circadian responses may differ in phase or degree, from the circadian processes that are generally accepted or empirically observed in the population at large. Depending upon circumstances and subject to confirmation, several specific examples might benefit from better-controlled lighting. Until now, however, circadian interventions have been developed for the laboratory and technology to bring these interventions out of the lab has not been available.

The present invention remedies this situation by providing light control and behavior- or illumination-sensing hardware to permit practical study and application of circadian effectors to aspects of training, lodging, industrial lighting, human activity and other systems.

By way of background understanding of relevant physiology, we begin with a description of sleep regulation.

The patterns of sleep/wake and the distribution of stages within sleep are understood using a theoretical framework termed the two-process model of sleep/wake regulation. At the heart of this model are two biological systems: a sleep-dependent homeostatic process (Process S) and a sleep-independent circadian process (Process C). Process S rises during waking and declines during sleep; Process C derives from the internal daily biological rhythm or oscillation. Under ideal circumstances, the result of the interaction between these processes is that sleep is favored after wakefulness accumulates across the day (Process S) and also at specific times in the 24-hour day (Process C); however, many occupations (i.e., military, professional sports, medicine) expect employees to perform critical operations following inadequate sleep or at adverse circadian phases (e.g., during biological night) or when inadequate sleep is combined with adverse circadian phase.

Systems of the present invention use knowledge of circadian biology to improve performance through either stabilizing circadian rhythms or aligning circadian peak of performance of a subject or of a group of subjects to performance schedule (e.g., military mission, professional sports game) or aligning circadian rhythms with scheduled performance in order to avoid the nadir of circadian performance. Circadian rhythms are ~24-hour cycles in human physiology that cause events such as sleep, alertness, mood, hormone release, etc. to be favored at certain times of the day. A misalignment between these endogenous circadian rhythms and the environment results in unpleasant side effects similar to those seen in jet lag and shiftwork.

Light is the most potent stimulus to entrain and shift circadian rhythms, and several components of light are critical in order to effectively alter the circadian timing system. The components include the spectral characteristics, the intensity, and the timing of light. I think we should add something here about photic history. The history of timing and intensity of light exposure is also important. Several studies have shown that the mammalian circadian system is most sensitive to light with spectral content near 460 nm and the phase shifting effect of light occurs at eye-level illuminance levels starting at about 50 and plateauing at 550 lux using white light, with greater phase shifts at higher intensities. Finally, the timing of light is critical based on whether an advance (light in the late biological night/early morning) or a delay of the circadian timing system (light in the evening) is targeted. Thus, several lines of research demonstrate that the appropriately timed delivery of light with specific spectral characteristics and of an ideal illuminance/intensity is a powerful tool for aligning endogenous circadian rhythms to the external environment/shift circadian rhythms; conversely, inappropriate timing of light can be an equally powerful tool in disrupting human circadian rhythms. Therefore, it is critical for circadian-enhanced biophilic lighting to be designed with informed circadian rhythm/sleep and engineering expertise to ensure optimal delivery (e.g., circadian alignment to performance schedule).

SUMMARY OF EMBODIMENTS

An aspect of the invention provides a system for tuning, control or remediation of a biological light-responsive state, the system comprising a lighting unit or light controller to control an illumination source and being operative to set at least one of: spectral distribution, light intensity, and a bioactive spectral band, during a programmed or specified time, so as to modify or supplement ambient or other illumination and set, shift or entrain a circadian biological response of a subject in a manner effective to enhance user health or performance. The system acts on circadian phase of a subject under changing, disrupted, unnatural, geographically discontinuous or spectrally deficient or otherwise non-optimal or inappropriate lighting. Aspects of the invention involve applying an illumination recipe that compensates for deficiency, or shifts or enhances the circadian response in a subject. The subject is generally a human but may be any mammal, bird or animal having visual apparatus that includes suitably light responsive cells.

In a particular embodiment, the system further comprises a Table of Prescriptive Settings for controlling light to synchronize a subject's timing or level of production of melatonin or other circadian effector to optimize at least one of alertness, cognition, physical performance, sleepiness, sleep, and restedness in accordance with a predetermined scheduled event, group activity or mission. In general, the controller provides automated control or wireless management of illumination parameters. In various embodiments, fully wired systems may be provided that incorporate a controller for a fixed environment or user population. For example, the controller applies a palliative light recipe to manage or reduce sleepiness, fatigue or tension, or to address a medical condition such as elevated blood pressure or to correct or alter a psychological condition, or a mood. The control subsystem may connect with a light monitoring and evaluation unit to detect sub-optimal ambient light conditions, which are then supplemented or corrected by one or more prescriptive settings.

In general, systems of the invention are designed with electrically efficient solid state light sources, and the controller controls a set of at least two distinct LED light sources to set a prescribed illumination supplement and/or schedule. Exemplary LED light sources include a blue-enhanced output band and a second band having little or no blue component. Such sources are commercially available, for example, the Hue smart lighting modules made by Philips Lighting.

The controller in various embodiments receives a sensor input, such as a biofeedback signal indicative of a subject's circadian state (phase) or estimated circadian state or physiological response (e.g., indicative of activity level or indicative of melatonin level in a subjects' body fluid or of one or more secondary biological or metabolic indicators of circadian state) and adjusts the light actuation recipe in accordance with that signal, altering ambient lighting to achieve a desired response in the subject. For example the subject having at least one scheduled performance obligation such as; an athletic event or team activity; a military mission which is an activity such as an army or air force mission or orders specifying an activity under which a naval pilot navigates; a medical activity conducted by any of the medical personnel such as in an emergency room schedule, a surgical or an obstetrical activity; an artistic activity such as a theater or concert performance; or a transportation endurance activity such as long distance trucking or jet plane travel. In any of these activities it may be necessary for the subject to use the system provided herein to operate under abnormal constraints of time and lighting, such as extending a work interval to an 80 hour shift; or a pilot flying repeat missions. In accordance with one aspect of the invention, the system controls ambient lighting to shift the circadian phase in such cases to one that is compatible with the expected or scheduled levels and times of activity of a subject—i.e., the systems herein are configured and operated to manage physiological responses to the time constraints.

Accordingly, the system according to this aspect of the invention, may be located in a designated remediation area of a structure or facility selected from: an athletic facility, an airport hangar, a compartment or a cabin of a truck, plane, ship or bus, a room in a hospital such as an interns' lounge, or an operating room, nursing home, or an assisted living facility; or a school class room, or a long-distance transport vehicle.

In an embodiment of the system, the controller and the LED light sources are in a kit in a container which is portable and further comprises instructions for installation and de-installation. In a certain embodiment, the automated control is manually adjustable by the subject or other user. In an alternative embodiment, the automated control is not adjustable.

Specific embodiments of a system may be adapted to address a specific performance environment, such as a classroom, an industrial production line, a long distance transport, or other user locus. Other embodiments may supplement existing level of ambient light to achieve circadian enhancements or synchronization, and still other embodiments may deliver a regimen of blue-enhanced illumination to compensate for age-related reduction of light-transmission characteristics of the user's eye, or inadequate or poor distribution of light in the working environment, or group-related behaviors that otherwise would impact normal diurnal rest or activity patterns.

Systems of the invention are based upon the strong connection between light and physiological circadian rhythms. Three components of light are critical in order to effectively alter the circadian timing system. The components include the spectral characteristics, the intensity, and the timing of light. Also knowledge of prior light and sleep/wake history and current light history helps. Several studies have shown that the mammalian circadian system is most sensitive to light with spectral content near 460 nm and the circadian phase shifting effect of light occurs at eye-level intensities (illuminance) starting at about 50 and reaching a plateau at 550 lux (white light), with greater circadian phase shifts caused by higher intensities. Finally, the timing of light is critical based on whether an advance (light in the late biological night/early morning) or a delay of the circadian timing system (light in the evening) is targeted. Thus, several lines of research demonstrate that the appropriately timed delivery of light with specific spectral characteristics and of an ideal intensity is a powerful tool for aligning endogenous circadian rhythms to the external environment; conversely, inappropriate timing of light can be an equally powerful tool in disrupting human circadian rhythms. Therefore, it is critical for circadian-enhanced biophilic lighting systems of the invention to be designed by informed circadian rhythm/sleep and engineering experts to ensure delivery that is effective (e.g., that aligns circadian phase to a performance schedule or actual ambient timing, or that stabilizes, normalizes or shifts the circadian phase).

SUMMARY OF THE INVENTION

A smart biophilic lighting system delivers circadian-targeted lighting that results in circadian stabilization to the local solar light dark/cycle or that shifts the circadian pattern to a target performance cycle or level of circadian activity. For example, if an East Coast sports team has to adjust to a California game or US military has a mission overseas, the systems of the invention are actuated to provide supplemental illumination that results in alignment of the subject's circadian clock with the prevailing daylight or natural circadian alignment. As mentioned above, current industrial or domestic lighting "systems" lack both the algorithms and hardware necessary to deliver appropriately timed circadian-affecting illumination. Some potentially suitable hardware components (LED lights, controllers, sensors, etc.) that could be used to assemble such a system are already available in the marketplace; however the art and science of combining them according to sound chronobiology principles and data so as to positively affect circadian performance has not yet been achieved. Solutions are proposed herein that address the weaknesses in current systems, (namely, the lack of clinical/chronobiology validation and the lack of suitable sense-and-control set points and operating capabilities to implement circadian targeted lighting), and achieve fully integrated, smart, circadian illumination to enhance the success of critical operations where performance goals require alertness and responsivity. Exemplary applications include athletes/sports teams, the military, and other mission- or performance-critical work. The present invention utilizes sensing and control to effectively measure and adjust the circadian phase of a subject. The application of dynamic sensing and control of lighting conditions to provide circadian-enhanced illumination is novel and represents a great advance in the design of functional interior lighting. This approach leverages new technologies in integrated and networked sensor modules, distributed network technology and environment awareness algorithms to address a problem that had not yet been tackled, namely that of achieving human-centric illumination that optimizes the performance and alertness of a subject in spaces and applications where performance is critical.

In overall summary, systems of the invention may have sensors that measure or indicate circadian phase data and sleep/wake patterns or history and may use the sensed data to select or calculate light recipes to shift/stabilize the circadian system to enhance performance and focus and sleep outcomes at specific/desired times.

This is done by shifting internal circadian phase to peak circadian time of performance (e.g., biological day) to match the external scheduled time of performance (e.g., biological night). Alternatively, the lighting system can shift the internal circadian rhythm to avoid circadian troughs in performance during externally scheduled work periods. In a circadian aligned individual the circadian rhythm in performance favors better performance during the day and worse performance at night. This lighting system can shift an individual's internal circadian time from biological day to biological night to match their work period that's scheduled at night. This is done by applying a suitable light recipe.

The recipes consist generally of sequences of light stimuli that are administered using ocular light exposure at specific times relative to circadian phase, and that contain certain spectral and illuminance characteristics. These times of delivery are informed by various factors, including the phase response curve, photic/light history, sleep/wake history, individual and group characteristics (age, sex, lifestyle, health condition, level of activity), work environment. Actual recipes may be limited by the flexibility (or lack thereof) to facilitate shifting internal biology by also shifting sleep/wake times or photic history, and the length of time available for the shift to take place.

Certain specific light characteristics, such as the amount of spectral overlap of the light source with the melatonin action spectrum—namely, the circadian action factor (CAF) and circadian efficacy of radiation—help inform the synthesis of the recipes and optimize the efficacy of the light stimuli; light stimuli with large CAF values are more efficient at imparting circadian phase shifts than light stimuli with low CAF.

To shift the circadian phase, the system must first be able to estimate it. This may be dome by means of any one of the methods currently available for measuring or estimating circadian phase, including core body temperature, dim light melatonin onset or levels) assessments or cortisol from saliva, blood, or urine, metabolites measured from body fluids, sleep/wake patterns (self reported or objectively recorded using from activity/inactivity measurements (e.g., actigraphy) or from PSG measured sleep, etc) or measured from contrasting light/dark photic history or from work schedules or travel schedules or a combination of the above factors.

Several experiments have demonstrated the ability of our lighting system and recipes to shift internal circadian biology in humans. One experiment was conducted in the laboratory in young adults. The aim of the study was to determine what spectral boost in white lighting (red, green, blue) and what intensity (low, medium, high) was best at suppressing melatonin. Data from 24 individuals was analyzed and these data demonstrated that the blue-boosted high intensity light was best at suppression of nighttime melatonin.

A second experiment was conducted in the laboratory in a mock classroom setting in middle school students. One aim of the study was to determine if spectrally boosted light significantly advanced circadian phase and whether it was associated with improved performance. Data from 8 middle school aged children showed that blue-boosted high intensity light advanced circadian phase with 5-days of morning exposure to the blue-boosted light compared to baseline. In addition, performance was enhanced on a memory recall task and subjective sleepiness reduced in the blue-boosted light condition compared to a red-boosted white light condition.

A third experiment was conducted in a real-world setting at a middle school, where the aim of the study was to determine if blue-boosted morning light could advance circadian rhythms in middle school students in the real world. Baseline circadian phase was measured using dim light melatonin onsets (DLMO) after 5 days of lighting as usual and compared the measurements within individuals to their DLMO following 5 days of blue-boosted morning light and blue-reduced afternoon light. Data from 16 middle school children showed that blue-boosted lighting was able to advance circadian phase when exposed to an average of 11 hours of blue-boosted morning light across the 5 day school week. In addition, the blue-boosted lighting condition was associated with a significant reduction in sleep onset latency (in other words, the children fell asleep more quickly).

A fourth experiment was run in adults in a real-world setting, a personal residence. The aim of the study was to determine if one administration of lighting in a real-world setting could delay the internal circadian clock. Data from 4 adults showed that the lighting system installed in a personal residence was able to delay circadian rhythms.

On a hardware level, the system consists of three basic components (1) illumination such as a multi-channel LED light module capable of delivering tunable spectrum and intensity; (2) sensor modules for obtaining occupant/subject information and enabling operation in feedback mode; (3) a networked control infrastructure based on a human circadian response "model" from which the optimal lighting conditions will be derived and the parameters of which will be updated based on sensor data for determining future behavior.

Preferably a software infrastructure is developed to achieve ambient occupation awareness via data mining from sensors, without invading the privacy of the occupants (e.g. image and sound recording are not used in the algorithms). This data may then be is used along with user-parameter input to derive and implement ideal, mission-critical lighting conditions from human models of circadian-phase alignment currently under development by the inventors. In operation, implementation of the circadian lighting is constantly tracked by the system's sensors and data algorithms, and system/model parameters are updated in real-time feedback mode from measured data. An initial period of operation may be devoted to identifying the "natural" circadian phase/light response characteristics of a subject or identified population (such as children, industrial workers, elderly nursing home residents) so as to effectively document control conditions and light-caused responses of the subject populations. As described further below, systems of the invention may include light-based or actigraphy-based subject diagnostic systems; site-based evaluation systems, therapeutic or otherwise improved illumination systems, as well as a general workplace programmable illumination control or improvement apparatus.

The system is intended to operate in a seamless manner—once the desired circadian alignment parameters (e.g., the time zone to adjust from and the time zone to adjust to) are entered into the system by the user, system operation begins and occurs automatically in the background detecting site illumination levels and user physiological circadian state or phase, and supplementing ambient illumination without the need for user intervention during the phase-shifting or illumination-supplementing process. The system does not shock the users by producing abrupt changes in the lighting conditions—rather, changes are gradual and allow the users to continue their normal activity while the system is at work shifting their circadian phase to meet travel, local or work-imposed change requirements.

BRIEF DESCRIPTION OF THE DRAWINGS

FIG. 8A and FIG. 8B illustrate CER or ambient light at different times of day and corresponding CER of illumination generated by the system of the invention.

FIG. 11. Spectra of LED channels used in our modules. Data were measured with a spectrophotometer by placing the modules within a white box. The blue, purple, and yellow curves represent typical LED emission spectra. The orange curve represents a phosphor-LED module, where the broadband phosphor emission is excited by the narrow LED peak near 450 nm.

DETAILED DESCRIPTION

Figure 1:
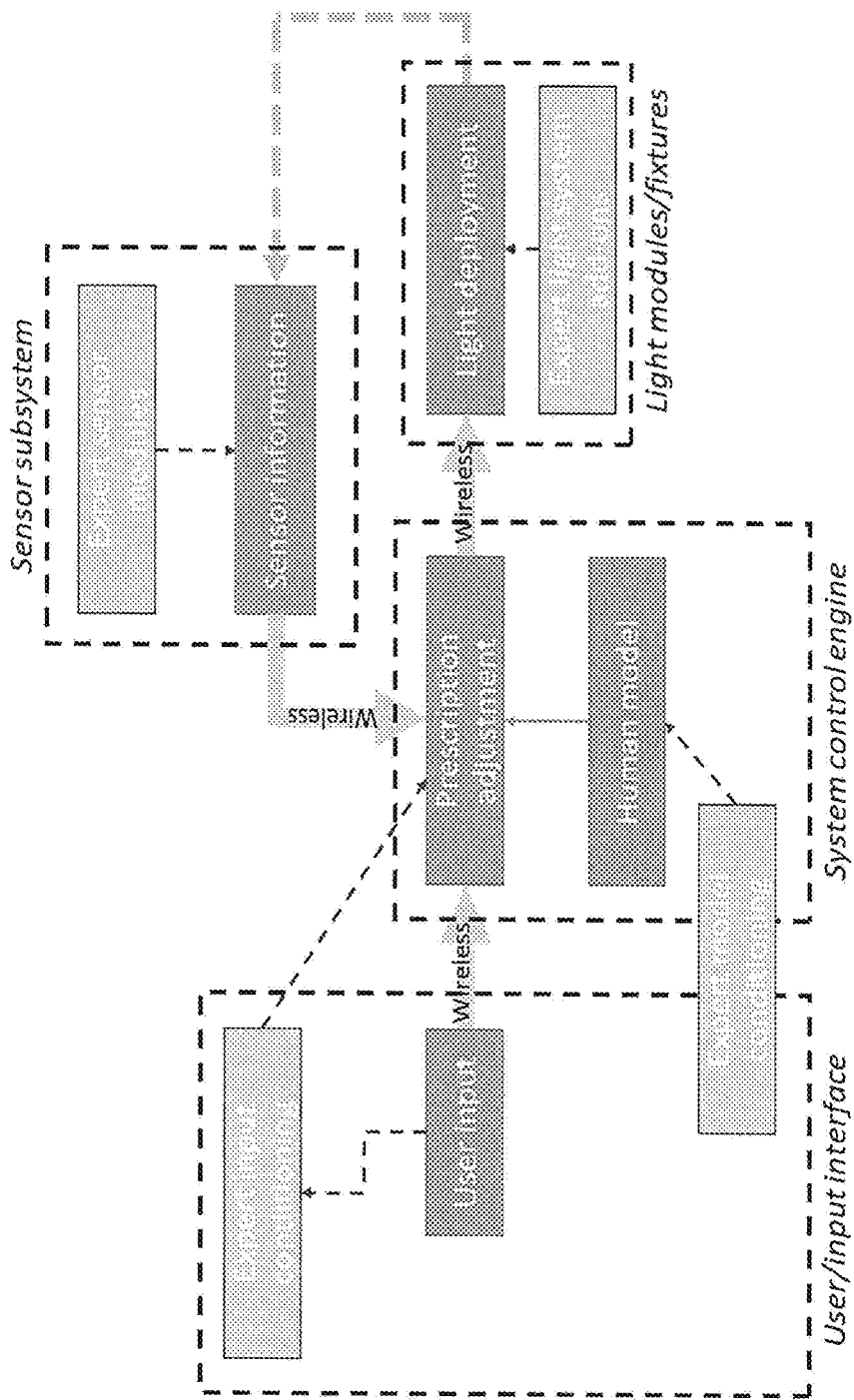
FIG. 1 is a schematic illustration of the system showing various components.

FIG. 1 is a schematic illustration of the system showing various components. A user input/interface and a sensor subsystem communicate with a control subsystem/unit, which in turn manages operation of a lighting system. The thick arrows marked "wireless" represent connections between subsystems which in one embodiment are preferably made using a wireless protocol such as WiFi, but may be implemented using conventional wired connections such as Ethernet etc. The boxes labeled "expert" connected with dashed arrows represent advanced features that embody control processes or application-specific light intensity, duration or spectral control and may involve expert consulting, may incorporate research findings, or may be implemented with machine learning to provide confirmatory or learned observations obtained from the system sensors such as actigraphy sensors worn by a subject and operating in a specialized subject group where specific behaviors become manifest via the actigraphy data.

Briefly, the system implements, or tunes, or documents a human model for circadian-photo-entrainment, or light-mediated establishment of a circadian pattern, which is partly derived from past experiments historically conducted by the proposers as well as other research groups, both in the laboratory and in-situ. This model is a central component of our system, as it enables computation of the appropriate light supplements or 'prescriptions'—i.e., combinations of spectral and intensity content as a function of time—and their effect and characteristic delays they promote to either stabilize or to actively shift the circadian phase of a user. However, in accordance with one aspect of the invention, physiological sensors worn by a subject are also monitored, and these may confirm the effectiveness of an applied light regimen, or may identify actual circadian data or phase advances/delays between illumination and response for a given group of subjects, or may display other newly-detected correlations.

For example, when applied to a control group of nursing home occupants, or applied to a group of middle-school children, or to a group of autism-spectrum children the sensors may demonstrate or approximate actual melatonin-sensed DLMO trough timing characteristic of the specific group of subjects, which may depend on factors such as the spectral transmissivity of their eyes, (for elderly or cataract patients) developmental factors affecting normal melatonin synthesis, or factors specific to peculiarities of cerebral development of the subjects.

Applicant expects that by applying the light control system and sensor arrangements described herein, operation will quickly identify many physiological and behavioral traits influenced by, or even determined by light-responsive melatonin levels, and identify one or more light correction or supplemental lighting, as well as the necessary time, duration and spectral intensity of light administration, required by the group for effective circadian phase management. Thus the systems of the present invention provide a scientifically valid measurement system to define recipes for circadian monitoring and control in human groups.

The human model begins with a circadian goal (e.g., to detect, to phase shift or to stabilize circadian rhythms) and uses baseline information from before (up to several weeks) the circadian goal is achieved (i.e., baseline dim light melatonin onset (DLMO), sleep, sleep/wake schedule, objective sleep tracking data) to inform a prescription for achieving that goal.

The ability of the described system to achieve circadian goals is being verified with circadian phase data collected from human participants as described further below. Circadian goals include but are not limited to achieving a circadian phase of peak alertness/focus, cognitive function, physical performance, and sleep facilitation. The system also identifies the circadian trough of alertness/focus, cognitive function, physical performance, and sleep consolidation/function. The circadian phases associated with peak/trough of alertness, cognition, sleep consolidation, for example, are well documented. The system may focus on either the avoidance of the trough or targeting the peak circadian phase or a combination of both. A combination of factors dictate how the human system navigates between these states. Exposure to light and prior light history are important factors that dictate this progression. In certain circumstances the system is operated to implement changes in lighting for at least several days leading up to a phase shifting light exposure in order to maximize the effect of the light exposure.

Figure 2:
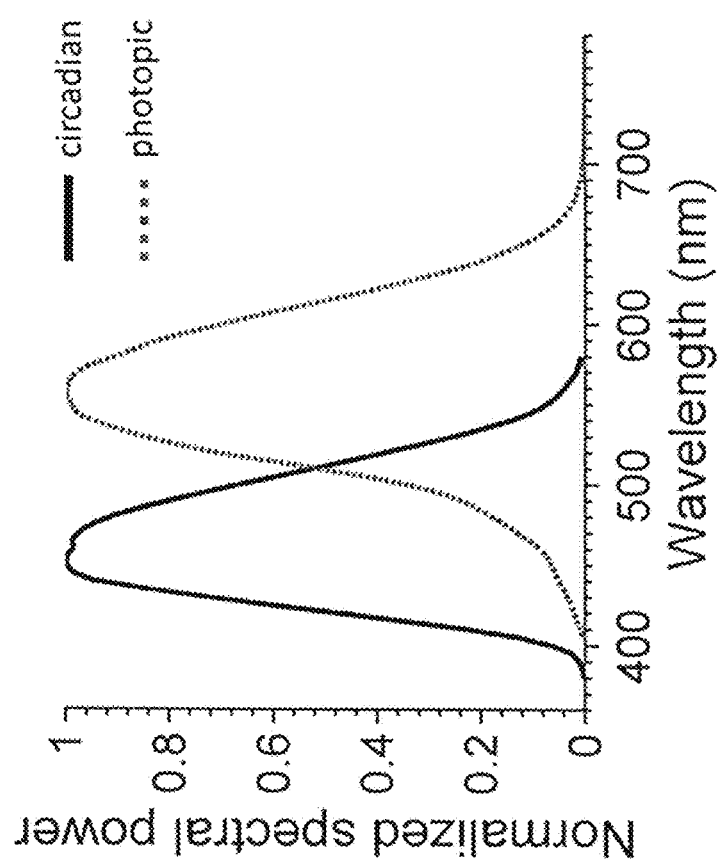
FIG. 2 illustrates the Melatkonin (circadian) and photopic spectra.

FIG. 2 above shows the Melatonin (circadian) and photopic spectra. The normalized action spectrum for melatonin suppression ($C(\lambda)$) and for photopic luminosity ($V(\lambda)$) shown for reference in that Figure are used to calculate the Circadian Action Factor (CAF).

Essential to system operation is the ability to control relative spectral output (i.e. power density) within the melatonin spectrum (FIG. 2) and outside of it, and in some instances to record or document the illumination history for use in the decision tree of the light control module. For example some useful control patterns may require boosting the blue component, and reducing the blue component, at different times of day. The relative output within and outside of the melatonin action spectrum can be quantified via the Figures of Merit described, for example, in Hye Oh, J., Ji Yang, S. & Rag Do, Y. Healthy. Natural, efficient and tunable lighting: four-package white LEDs for optimizing the circadian effect, color quality and vision performance. *Light Sci. Appl.* 3, e141 (2014). Recently, Oh et al. introduced two figures of merit, the circadian efficiency of radiation (CER, Equation 1) and the circadian action factor (CAF), to help quantify the circadian effect of artificial light sources. The CER quantitatively measures the portion of the source's spectral radiant flux that overlaps with the melatonin-suppressing action spectrum, and is therefore relevant for gauging the interaction of a light source with the circadian pacemaker. The CER is defined as the ratio of the circadian flux to radiant flux:

$$CER = K_{c0} \int_{380\,nm}^{780\,nm} C(\lambda)S(\lambda)/\int_0^\infty S(\lambda)d\lambda, \quad (1)$$

where $S(\lambda)$ is the spectral radiant flux of the lighting source and $C(\lambda)$ is the spectral circadian efficiency function (also called the circadian action function). $K_{c0}=683$ blm/W is the maximum value of the spectral luminous efficacy for photopic vision. FIG. 1 shows the circadian sensitivity function (i.e. the melatonin-suppressing action spectrum) plotted within the visible range. We used the data from Gall et al. in our experiments. The luminous efficiency (photopic) function is also shown for comparison.

The normalized action spectrum for melatonin suppression ($C(\lambda)$) and for photopic luminosity ($V(\lambda)$) are shown for reference. They are used in equations (1) and (2) to calculate the Circadian Action Factor (CAF), defined as the ratio of the CER to the luminous efficiency of the radiation (LER, Equation 2). The LER is computed similarly to equation (1):

$$LER = K_0 \int_{380\,nm}^{780\,nm} V(\lambda)S(\lambda)/\int_0^\infty S(\lambda)d\lambda, \quad (2)$$

where $K_0$ is 683 lm W$^{-1}$ V and $V(\lambda)$ is the photopic spectral luminous efficiency function. The CAF thus has units of blm/lm, i.e. 'biolumen per lumen', and thus represents the ratio of the source's luminosity within the circadian range to that within the photopic range.

Finally, closely related to the concepts of color and spectral fullness is the color rendering index (CRI). The CRI quantifies the ability of a light source to render the colors of illuminated objects faithfully in comparison with an ideal light source. The maximum CRI value is 100. LED-phosphor based sources often exhibit a 'dead-zone' or gap in the spectrum, occurring between the blue 'pump' emission and the phosphor emission, and generally spanning wavelengths between 460 and 530 nm.

Different CER and CAF are achieved in LED systems containing independently controllable channels (FIG. 3). Each channel has a different spectral output content. Combining multiple channels by driving them at different (adjustable) intensities e.g., such as via pulse width modulation, thus allows for additive combinations of the individual output spectra to generate a "sum" spectrum that combines spectral features from all channels being driven in the same proportions. In this manner, desired spectra for the purposes of interacting with the circadian system and for achieving desired CAF and CER values are "assembled" from basic components. The channels are either spectrally broadband (e.g. phosphor-LED) or spectrally narrow (e.g. as in a conventional non-phosphor LED), depending on whether they are used to patch (or boost) certain regions of the desired output spectrum or to create a baseline broadband spectrum. Combined, the channels should produce light within the visible range (from ~360 to 780 nm).

Broad-spectrum phosphor-LEDs can be combined to create a baseline spectrum devoid of spectral gaps. If needed, spectrally narrow LEDs can be added to shape certain regions of interest in the spectrum, such as the wavelengths corresponding to the melatonin action spectrum near 460 nm. Passive elements, such as absorbing or attenuating filters can also be used, but in this case efficiency is sacrificed.

Figures 3A, 3B:
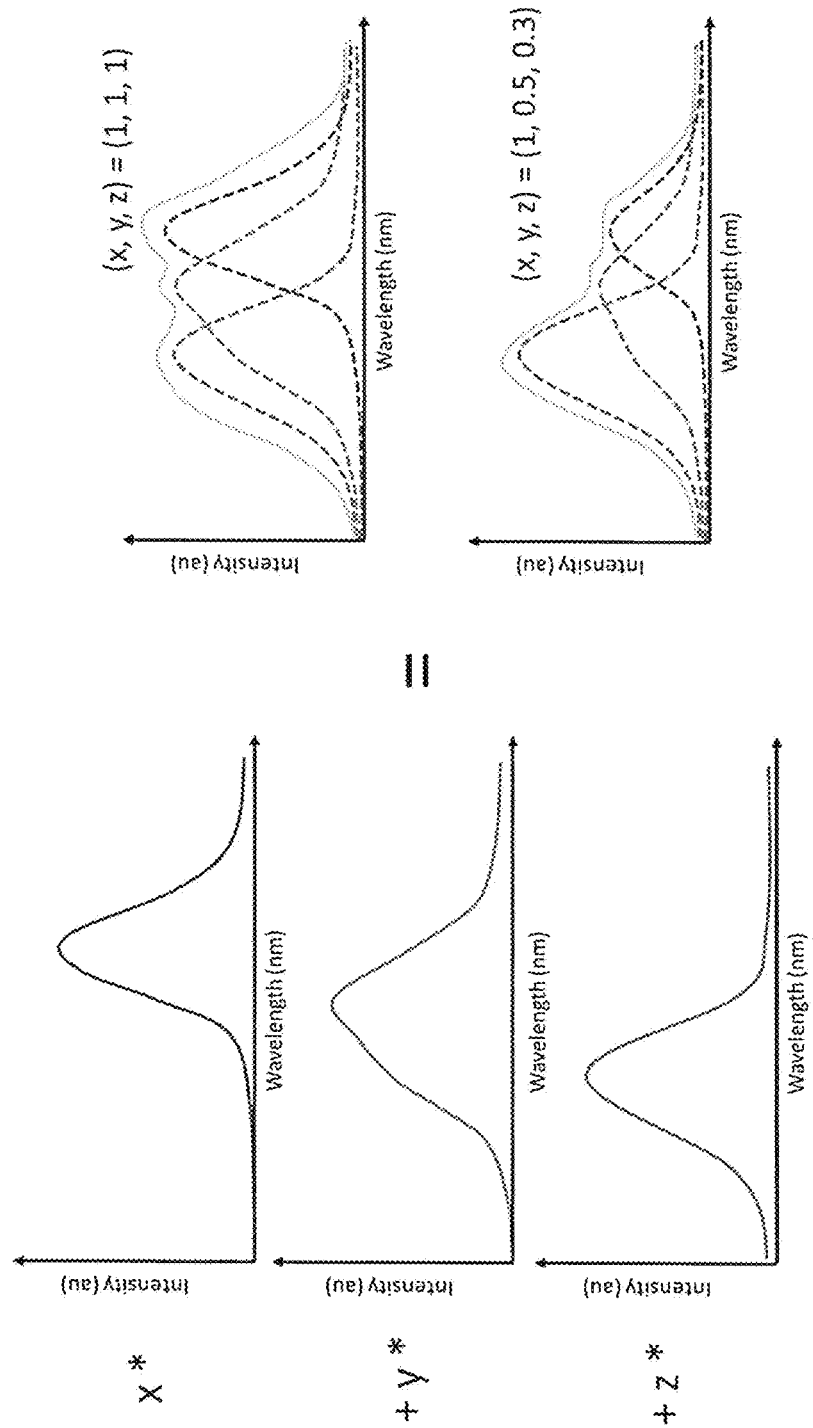
FIG. 3A and FIG. 3B illustrate creation of circadian enhanced spectra, wherein individual LED channels (FIG. 3A) are driven with different intensities (x, y, z) to produce different sum spectra (FIG. 3B).
Figures 4A, 4B:
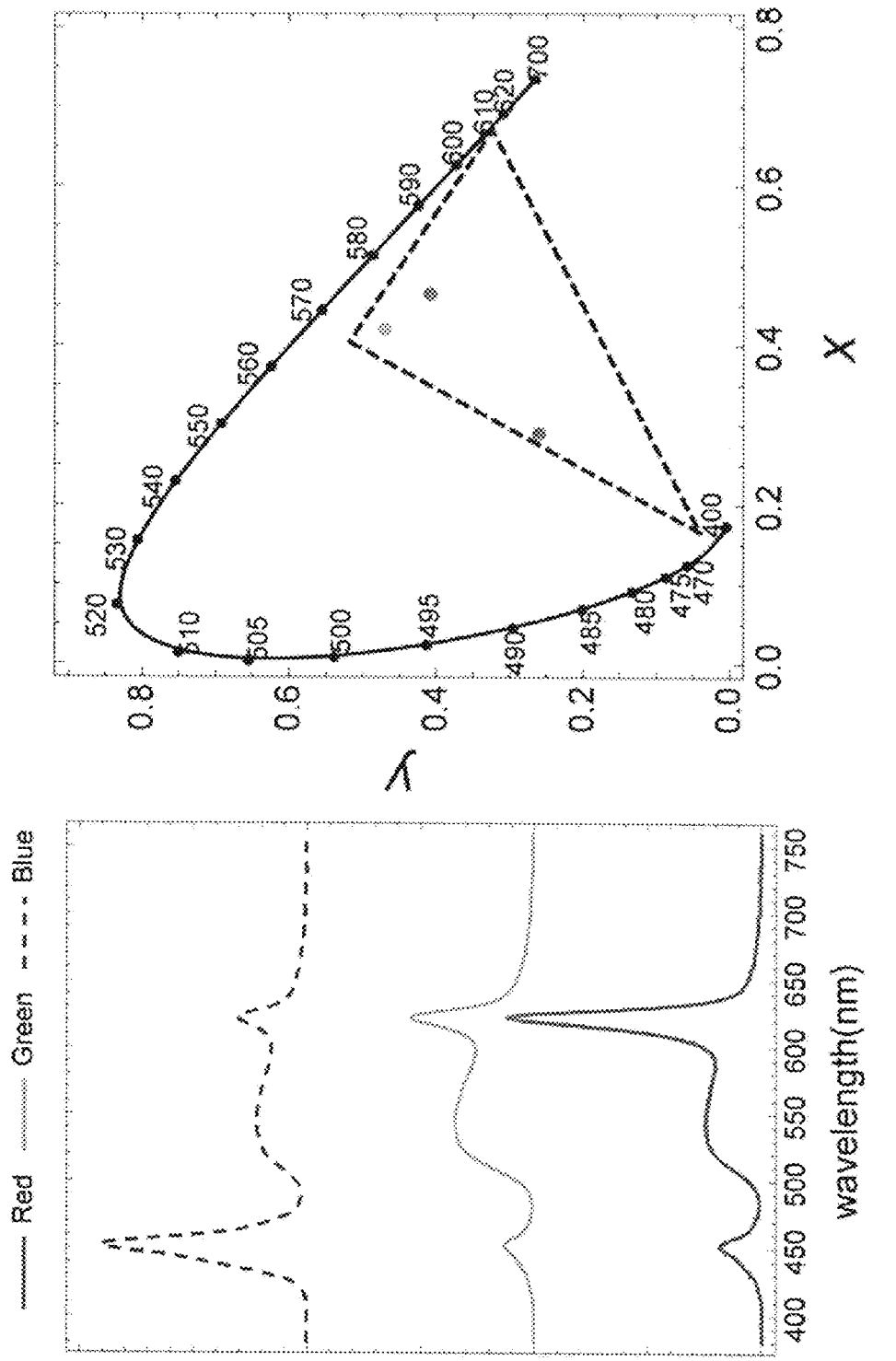
FIG. 4A shows Spectra of "Red", "Green", and "Blue" presets chosen for one study, the spectra being offset vertically and scaled based on the photopic illuminance (lux) for easier viewing.
FIG. 4B plots colors of spectra (FIG. 4A) in a chromaticity diagram for reference.

FIGS. 3A and 3B illustrate the method for creating circadian enhanced spectra. As shown in FIG. 3A individual LED channels are driven with different intensities (x, y, z) to produce different sum spectra as shown in FIG. 3B. FIG. 4A shows spectra of "Red", "Green", and "Blue" presets chosen for one study. The spectra are offset vertically and scaled based on the photopic illuminance (lux) for easier viewing. In FIG. 4B colors of the spectra of FIG. 4A are plotted in the chromaticity diagram for reference. Such systems are used in sleep-lab studies. The LED spectra of FIGS. 4A and 4B and were found to influence human circadian rhythms based on initial studies conducted by us. The LED spectra were created with off-the-shelf controllable LED lights (Philips Hue). Their CER and CAF values along with other figures of merit are given in Table 1 infra.

Figure 5:
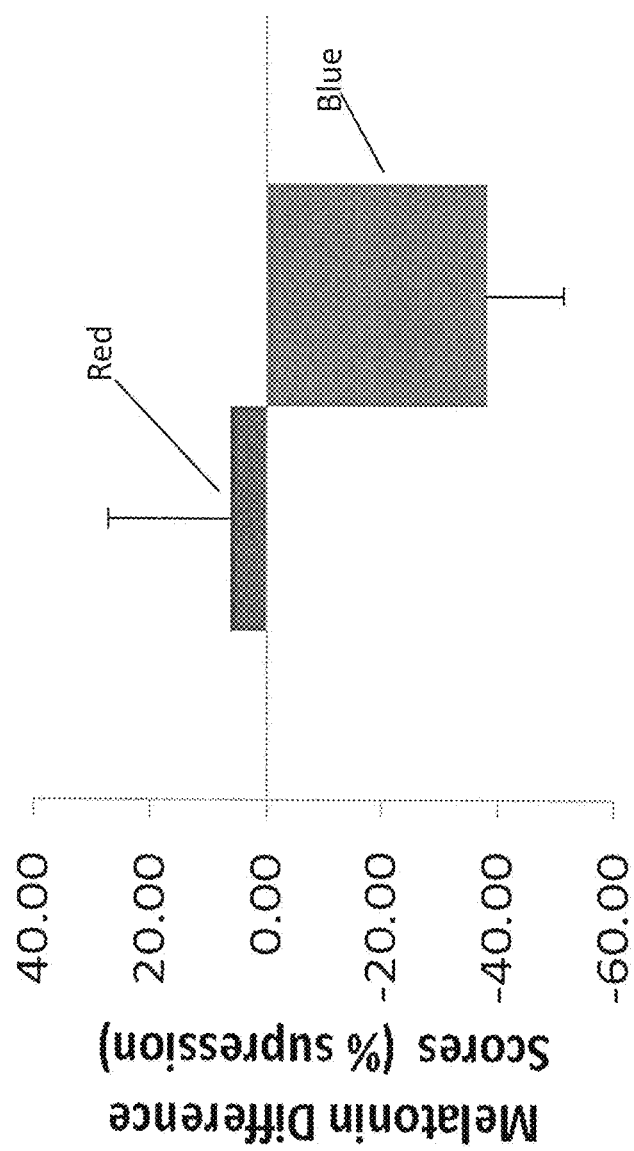
FIG. 5 shows (on the left side) the effect on melatonin of red-enhanced illumination and (on the right side) blue-enhanced illumination. A greater suppression of melatonin with blue boosted light at 500 lux was observed compared to red-boosted broad spectrum light. The results indicate that spectrally boosted white light can affect melatonin suppression and thus effectively interact with the circadian system.

FIG. 5 is a bar graph showing melatonin difference scores (percent suppression) resulting from exposure either to ambient light enhanced with bright light conditions (about 500 lux) of red wavelengths (bar on the left side of the Figure) or blue wavelengths (bar on right), of students exposed to the system herein. Light was administered beginning at 1.5 hours post habitual bedtime for one hour. The data indicate that the blue-enhanced light was more effective than the red-enhanced light (p=0.002) in suppressing melatonin, the percent suppression calculated in comparison to dim light conditions (less than 10 lux).

A greater suppression of melatonin with blue boosted light at 500 lux was observed compared to red-boosted broad spectrum light (F(2,14)=9.55, p=0.0024), and indicates that spectrally boosted white light can affect melatonin suppression and thus effectively interact with the circadian system of a subject.

Figure 6:
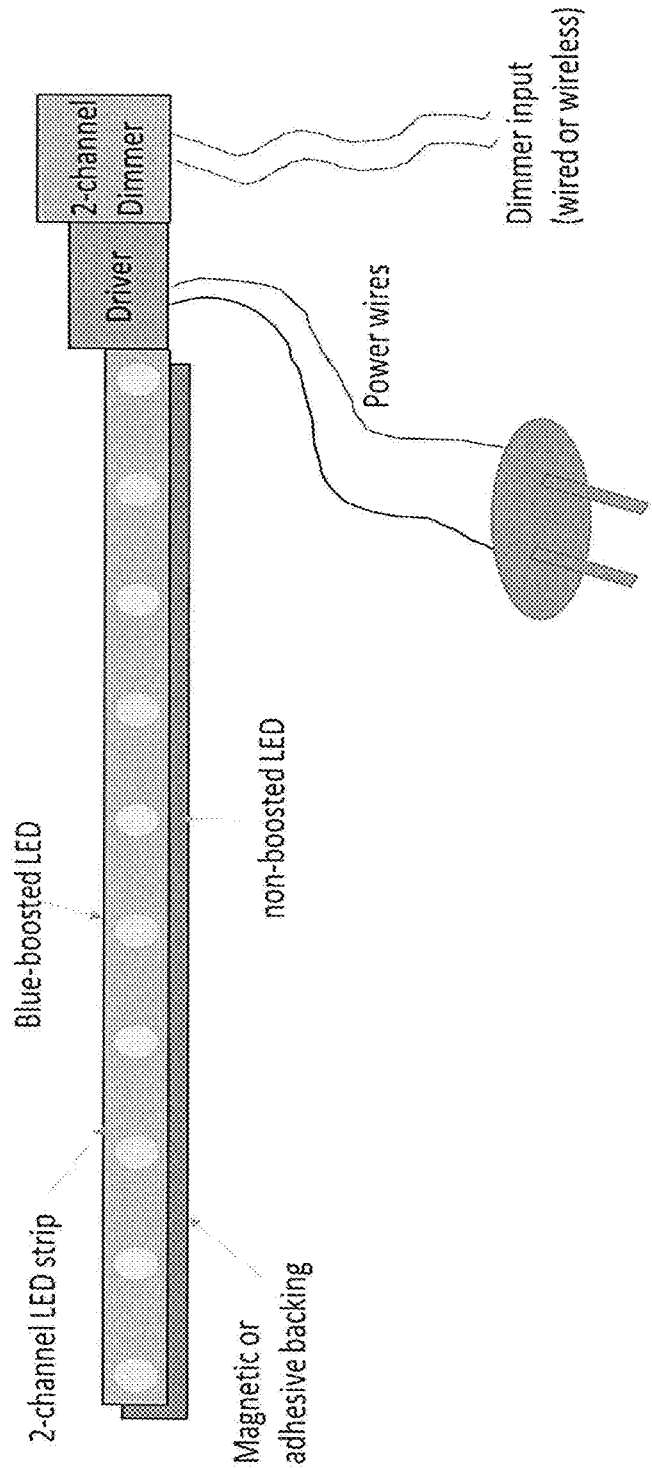
FIG. 6 schematically illustrates a portable, deployable, circadian-enhanced LED fixture for use in systems of the invention.

FIG. 6 is a schematic drawing of a portable, deployable, circadian-enhanced LED fixture for easy installation in critical environment without the need to perform significant structural changes. The fixture has two different spectral sources extending in a long strip or band for projecting illumination into a workspace, and may be mounted, for example, over a work bench or in multiple strips to provide room-filling illumination of controlled intensity and spectral distribution.

TABLE 1

Measured parameters for spectra used in study

| Spectrum Boost | Chromaticity (x, y) | CRI | CCT (K) | CER (blmW$^{-1}$) | LER (lmW$^{-1}$) | CAF (blm lm$^{-1}$) |
|---|---|---|---|---|---|---|
| Red | (0.464, 0.408) | 89.8 | 2487 | 100 | 423 | 0.24 |
| Green | (0.42, 0.47) | 74.9 | 3672 | 107 | 374 | 0.29 |
| Blue | (0.29, 0.26) | 79.1 | >6500 | 323 | 307 | 1.05 |

Further studies are underway to better ascertain and quantify these interactions. However, the results reported here serve as proof of principle that an off the shelf system can be effective for generating different light conditions that directly and measurably affect circadian phase. It is envisaged that systems of the present invention will be operated with several different populations and institutional environments to detect responses and sensitivities, and to develop useful conditioning or therapeutic regimens to improve subject health for specific individuals or groups.

This may be done by monitoring actigraphy data from group or individual to determine its characteristic circadian phase in its typical setting or location, and applying a light effector or stimulus, such as blue-boosted light at an identified time in the circadian phase, and determining from the sensor worn by the subject(s) how the stimulus delays, stabilizes or advances the establish circadian phase. The observed effects may be general, or may apply to specific groups of subjects or to individuals. On an elementary level, the light prescriptions may be established to delay, or to advance, the circadian phase. Furthermore fixed light-applying recipes may be provided in some circumstances without reference to the sensed responses of the subjects or groups of subjects.

By way of example, administration of blue-boosted light for several hours in the morning was found to advance dim light melatonin onset (DLMO), thus advancing the circadian phase. Studies of performance as measured by memory recall (# correct) or subjective sleepiness (using the Karolinska Sleepiness scale) were found to be influenced by daily administration of blue-boosted light in the mornings compared to red-boosted light. Blue-boosted light enhanced memory/recall scores, while red increases sleepiness.

FIG. 6 schematically illustrates one portable, deployable, circadian-enhanced LED fixture configured for easy installation in critical environment without the need to perform significant structural changes.

Systems of the invention may include a sensor system, which may include the following types of sensor units/tasks:

(1) Photometer units capable of measuring illuminance and spectral composition in the environment where the prescription is being implemented. This data is used in recalculating/correcting channel drive values derived from the human model in real time to compensate for variations in light composition due to (a) extraneous sources of light, including windows and other light sources not belonging to the system and (b) variations in the light output from the system illumination modules due to changes in temperature, etc.

(2) Human circadian activity sensors. These may include wearable and non-wearable devices capable of assessing the occupants' circadian activity. Wearable melatonin measuring devices (e.g. skin-patch, saliva-sampling, blood sampling), wireless core body temperature sensors, core body temperature probes, etc. Wearable accelerometer units (such as Actigraph, Fitbit, or custom made units) may be used for determining sleep-wake onset.

(3) Human physical and cognitive activity monitoring sensors, capable of assessing physical and cognitive activity levels in the occupants. This may include wearable devices e.g. wearable accelerometer, electroencephalogram (EEG) modules, etc. or indirect (non-wearable) units e.g. sound level measurements, sonar/radar motion sensors, infrared motion sensors, gas/CO2 sensing etc.

(4) Units equipped with other environmental parameter sensors, including temperature, humidity, etc. may also be used to derive auxiliary parameters for the human model.

Systems of the invention employ light prescriptions—lighting of defined intensity, spectral distribution and duration—which the control system uses to effect the desired operation. These may be general pre-defined prescriptions of a proposed or theoretical nature, or may be set up based on detected environmental or physiological states and operative to restore a desired physiological condition or to enrich or supplement the prevailing illumination.

Light Prescriptions.

For example, in order to achieve a rapid phase delay in the circadian phase of a subject, circadian-targeted light will be delivered at an appropriate time which may be determined from initial observations of the sensor system in operation, for up to several or more hours. The PRCs show that phase advances change to phase delays at about 3 hours before DLMO and switch from delay to advances at about 9 hours after DLMO in general.

Places of potential use for the system described herein include: athlete dormitories, residences and training facilities (e.g. athlete villages in the Olympics), military bases and barracks, military transport systems—airplane, submarines and ships, wellness clinics and hospital wellness centers, classrooms, and commercial transportation, addiction rehabilitation facilities.

Thus, the system has three basic components, as previously outlined has broad uses. The subsystems are—(1) a hardware component in the form of lighting fixtures/modules capable of delivering tunable lighting that is capable of stimulating the circadian system; (2) a hardware component in the form of distributed sensors capable of gathering occupant information and information on other sources of illumination, so that the system can correct its output in feedback mode and optimize the delivery of lighting conditions to the occupants according to the lighting-prescription requirements. (3) A software component that controls the hardware and provides a method for users to enter system parameters, such as desired times of peak performance, schedule constraints, etc. Based on this information, the software chooses and adapts one of its various default prescriptions (based on the human model parameters) to the specified timeframe, and implements it in the hardware front end. In addition to these three components, the system as envisaged here, entails the development of lighting-prescriptions for optimizing various aspects of human performance to various required tasks.

A lighting-prescription is a combination of specific lighting conditions that are implemented by the system over a period of time. These conditions include spectral, color, intensity and mode of delivery (e.g. direct vs diffuse, continuous vs periodic, time/frequency modulations, etc.) information. These lighting prescriptions are derived from knowledge of how the human circadian system operates, and therefore are designed in reference to the human model. Such knowledge is obtained from findings obtained in scientific/clinical circadian studies on human subjects.

Light-Prescription Details.

The light-prescriptions may be designed with the purpose of optimizing human performance in the subjects' living or working environment, or designed for better enabling mission-critical tasks to be performed at a geographic location offset in time or geography. Elements of human performance that can be improved with this system include focus/alertness, physical endurance and stamina, cognitive/learning capability, decision-making ability, problem-solving, etc. The specific content of the lighting prescriptions(s) can be considered as either (1) trade-secrets, (2) subject matter requiring further research or investigation to pursue in other separate patent filings, (3) as continuation-in-part (appendices/addenda, subdivisions) to this patent application. While general prescriptions could be produced now if case (3) is adopted, further laboratory circadian studies are believed to be generally necessary to validate the recipes relevant for desired effects to be achieved or specific uses. Indeed, because so many biological systems appear to be influenced by light exposure, even a routine search for and testing or simple light prescriptions will possibly result in surprising discoveries not readily deduced from the foregoing known results. In general different classes of subjects, when monitored and correlated with their light exposure and performance measurement circadian data, are expected to result in "discovery" of use-specific causal or health-related connections.

Light prescriptions can exist in two types—(1) general light prescriptions aimed at conditioning the circadian system of the users according to model input parameters such as desired time or start and peak of activity. These prescriptions are based on a global human model that is assumed applicable to all end-user instances. (2) Customized prescriptions aimed at optimizing the circadian activity to a specific group conducting a specific task, i.e., involving optimizations/personalization of the human model.

Prescriptions of type (1) are administered automatically by the system upon entry of the relevant parameters in the system's interface by the user, while those of type (2) may require periodic intervention from an expert in chronobiology. Prescriptions of type (2) may therefore require a periodic (e.g. subscription) ongoing evaluation and control software update service in addition to initial hardware acquisition of the basic system, and thus may require development of special expert consulting and implementation crews.

Embodiments of the system may include an item that is worn by the subject. For example, the system is an item that is eyewear, a headband, a cap or hat, or a headset. Sensors that measure circadian or biometric parameters, such as a Fitbit/apple watch, can also be worn. Advantageously, by integrating system components such that the subjects' circadian state is automatically monitored, detected and analyzed, the system may be configured so that detailed user expertise or expert set-up are not needed for many basic operation. Thus, the elements and representative characteristic operation shown in FIG. 1-FIG. 6 are of general applicability, and may even, in some embodiments be operated with a software-embodied learning module which adapts its operation to ambient conditions detected at the site of installation, detecting illumination patterns, determining user circadian phase, applying light supplements and detecting or confirming the systems' effectiveness at stabilizing or shifting the effect on the subject during its operation.

Briefly recapitulating the aforedescribed structure and described operation, of a basic system:

FIG. 1 shows four sets of components: a user/input interface which includes expert input conditioning are a first component; which can be transmitted wirelessly to a system control engine containing prescription adjustment and a human model; connected wirelessly to light modules/fixtures; which is connected to a sensor subsystem containing expert sensor modules and sensor information.

FIG. 2 shows normalized spectral power effects and circadian melatonin and photopic spectra as a function of wavelength (nm) on the abscissa.

FIG. 3A shows individual LED channels driven with different intensities.

FIG. 3B shows how different sum spectra are produced by the LED channels of different intensities in FIG. 3A.

FIG. 4A shows spectra of red, green and blue presets chosen for an example herein.

FIG. 4B shows colors of spectra of FIG. 4A in the chromaticity diagram.

FIG. 5 is a bar graph showing melatonin difference scores (percent suppression) resulting from exposure either to ambient light enhanced with bright light conditions (about 500 lux) of red wavelengths (bar on left) or blue wavelengths (bar on right) of students exposed to the system herein. Light was administered beginning at 1.5 hours post habitual bedtime for one hour. The data indicate that the blue-enhanced light was more effective than the red-enhanced light (p=0.002) in suppressing melatonin, the percent suppression calculated in comparison to dim light conditions (less than 10 lux).

FIG. 6 is a schematic of a portable, deployable circadian-enhanced LED fixture for easy installation, having magnetic or adhesive backing on a 2-channel LED strip which includes blue-boosted LED and non-boosted LED light sources.

In general the light systems herein are intended to and are capable of affecting circadian physiology, mood, biophilic properties, focus, wellness and health. One exemplary system may be operated to establish the baseline circadian states of elderly subjects in prevailing seasonal light.

Figure 7:
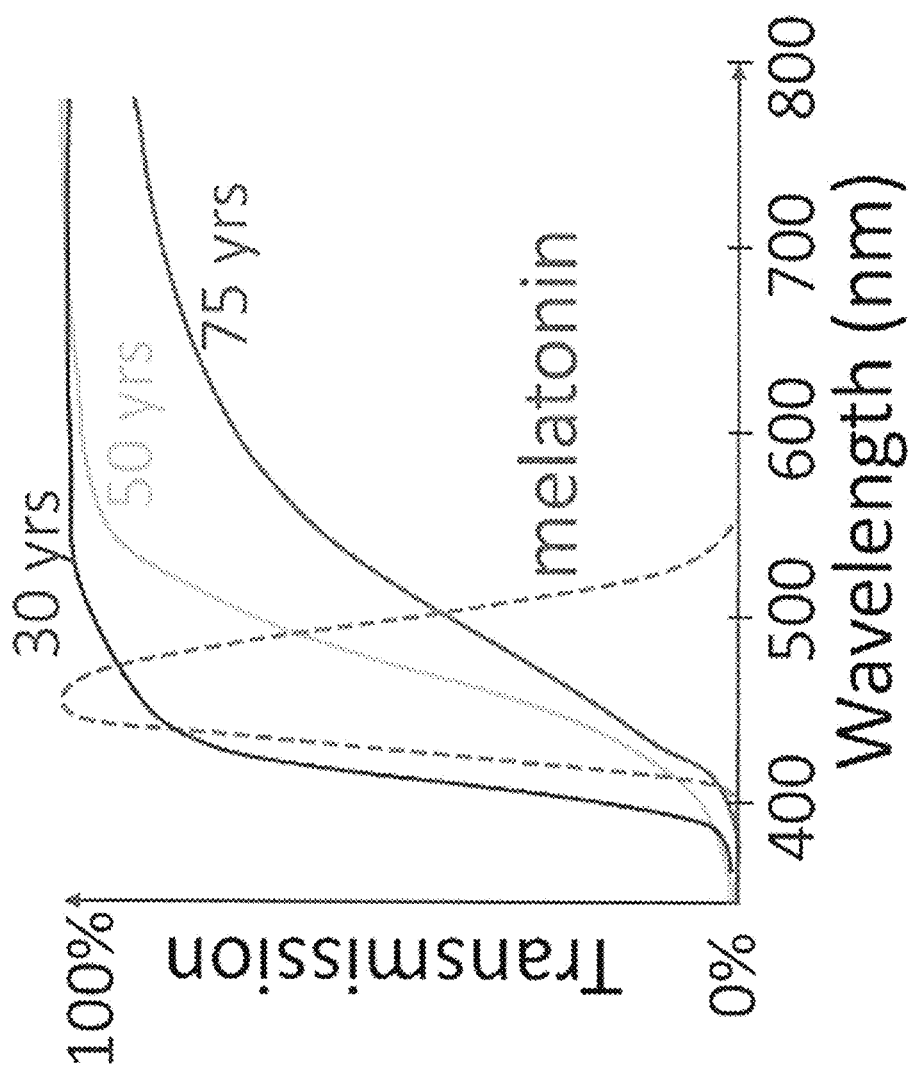
FIG. 7 illustrates changes in transmissivity of the optic lens with increasing age of a subject.

FIG. 7 illustrates the effective percent transmission of light in the eye reaching the retinal ganglion cells across the wavelength spectrum for aged human subjects of age 30, 50 or 75. Such subjects thus are effectively exposed to lesser illumination. Since their metabolic efficiency and capabilities for melatonin production as a function of wavelength, may also change significantly, the set points or LED recipes are expected to be quite different for such groups of subjects.

By way of example of what may be encountered in practice, FIG. 8A is an analysis of the circadian efficiency of radiation (CER) for sunlight measured Jun. 4, 2016 in Providence R.I. (black curve), also showing simulation of the natural lighting that is achieved with operation of a 2-channel LED troffer system.

FIG. 8B shows high and low CER spectra generated by the 2-channel system herein, and a comparison with the melatonin action spectrum.

Figure 9A:
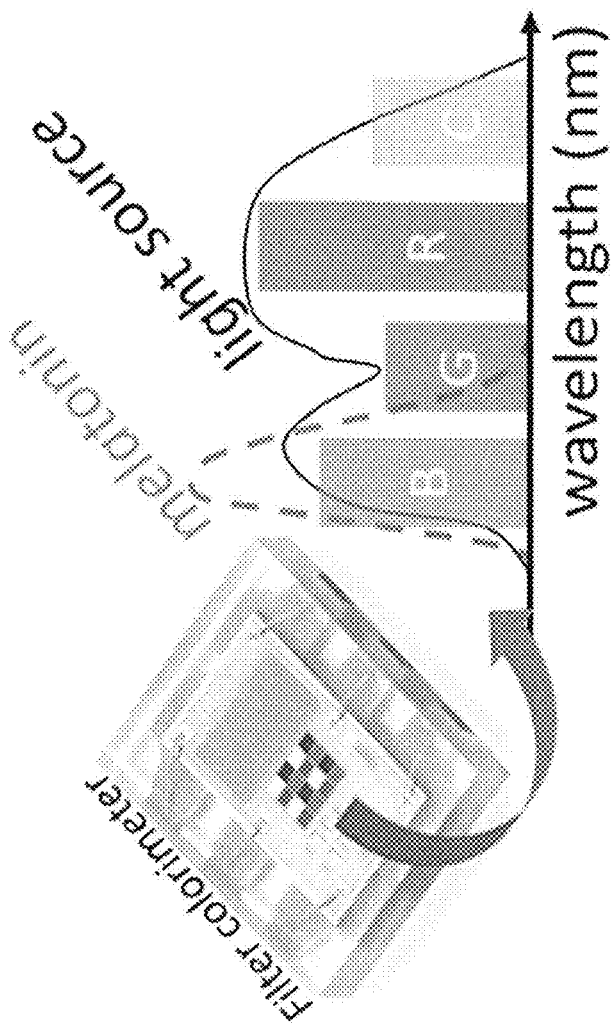
FIG. 9A and FIG. 9B show a photonic sensor and a wearable sensor units for collecting photonic and circadian information.
Figure 9B:
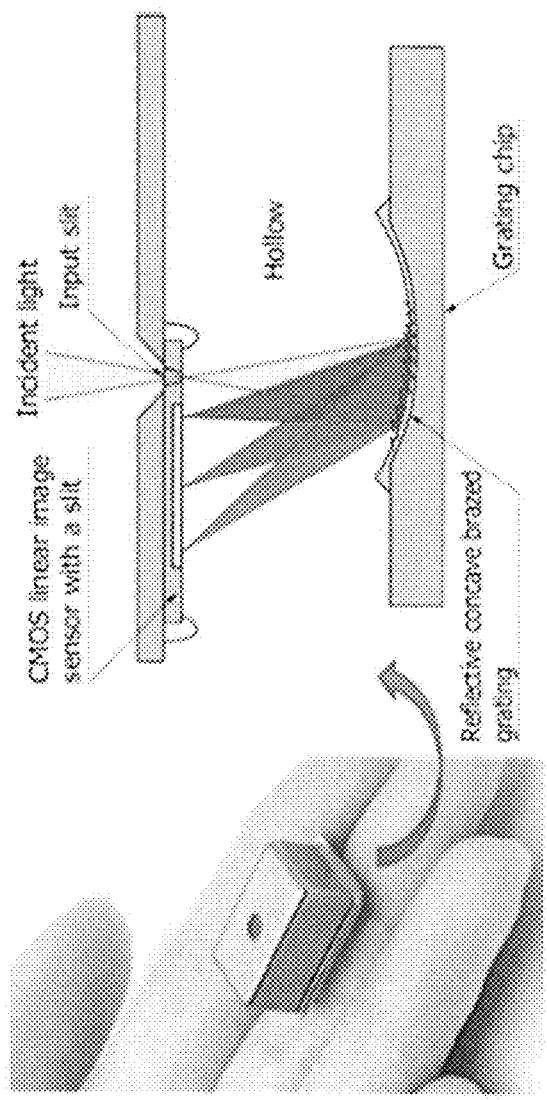

FIG. 9A and FIG. 9B illustrate photometer sensors and a low-cost on-chip filter colorimeter sensor that is useful in some embodiments to obtain and record a low resolution spectral characterization of the ambient light; and FIG. 9B shows an on-chip spectrometer that allows high resolution spectral measurement. These and other sensing elements may be incorporated in systems of the invention for measuring and determining the circadian and photopic light experienced by a user, which is then to be supplemented by a light prescription applied by the controller.

Figure 10:
FIG. 10 illustrates wearable sensor units for collecting user information and spectral distribution information which is processed or correlated with ambient conditions or lighting control operation to manage or strengthen the user model in a circadian lighting control system.

FIG. 10 is a drawing of one wearable sensor device showing a number of possible sensing elements that can be included in a user-worn sensor addressed to collection and monitoring of biometric data such as body temperature, heart rate, movements or activity, hours of sleep and rest in addition to the light exposure and spectrum characterization data.

Figure 11:
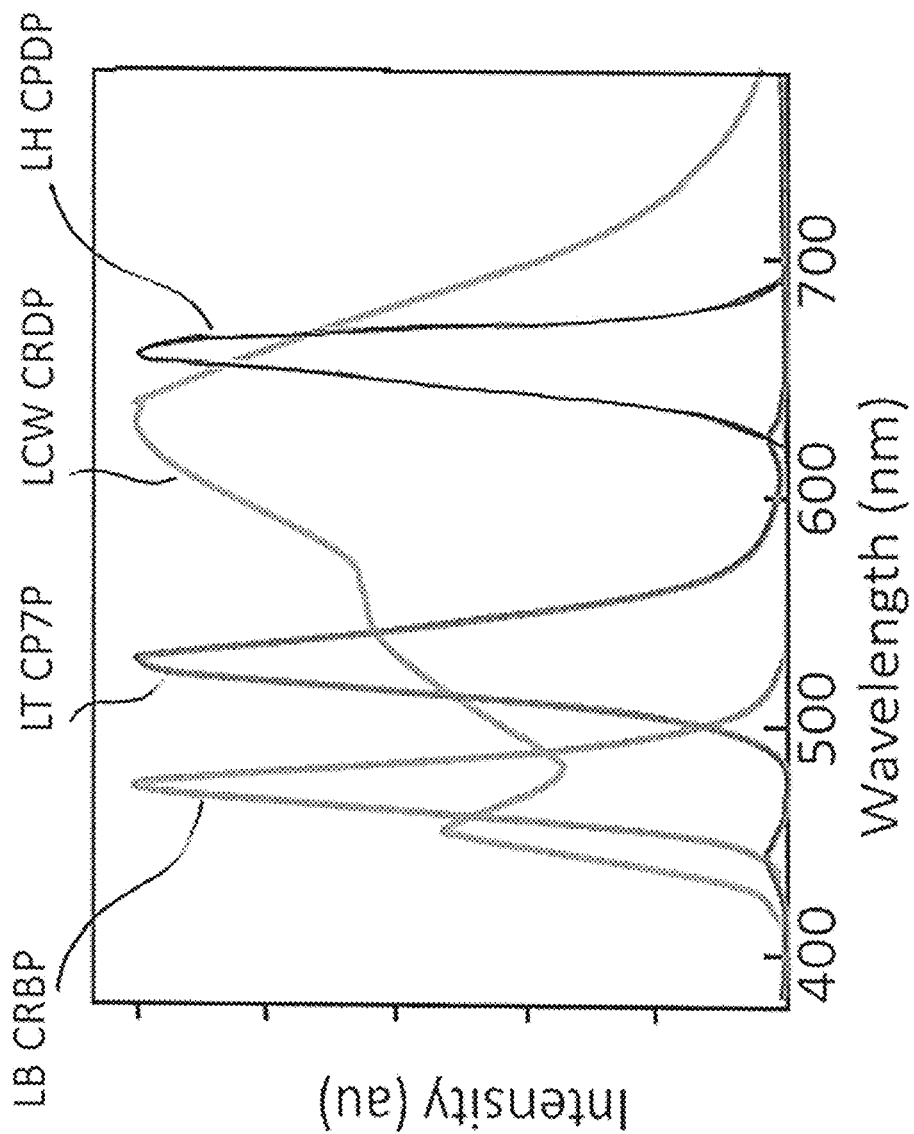
FIG. 11. Shows the Melatonin (circadian) and photopic spectra. The normalized action spectrum for melatonin suppression ($C(\lambda)$) [18, 20, 21] and for photopic luminosity ($V(\lambda)$) are shown for reference. They are used in equations 1 and 2 to calculate the Circadian Action Factor.

FIG. 11 illustrates spectra of LED channels used in modules of a prototype system to provide the appropriate spectral coverage. Data were measured with a spectrophotometer by placing the modules within a white box. The blue, purple, and yellow curves represent typical LED emission spectra. The orange curve represents a phosphor-LED module, in which broadband phosphor emission is excited by a narrow LED peak, shown near 450 nm.

Figure 12:
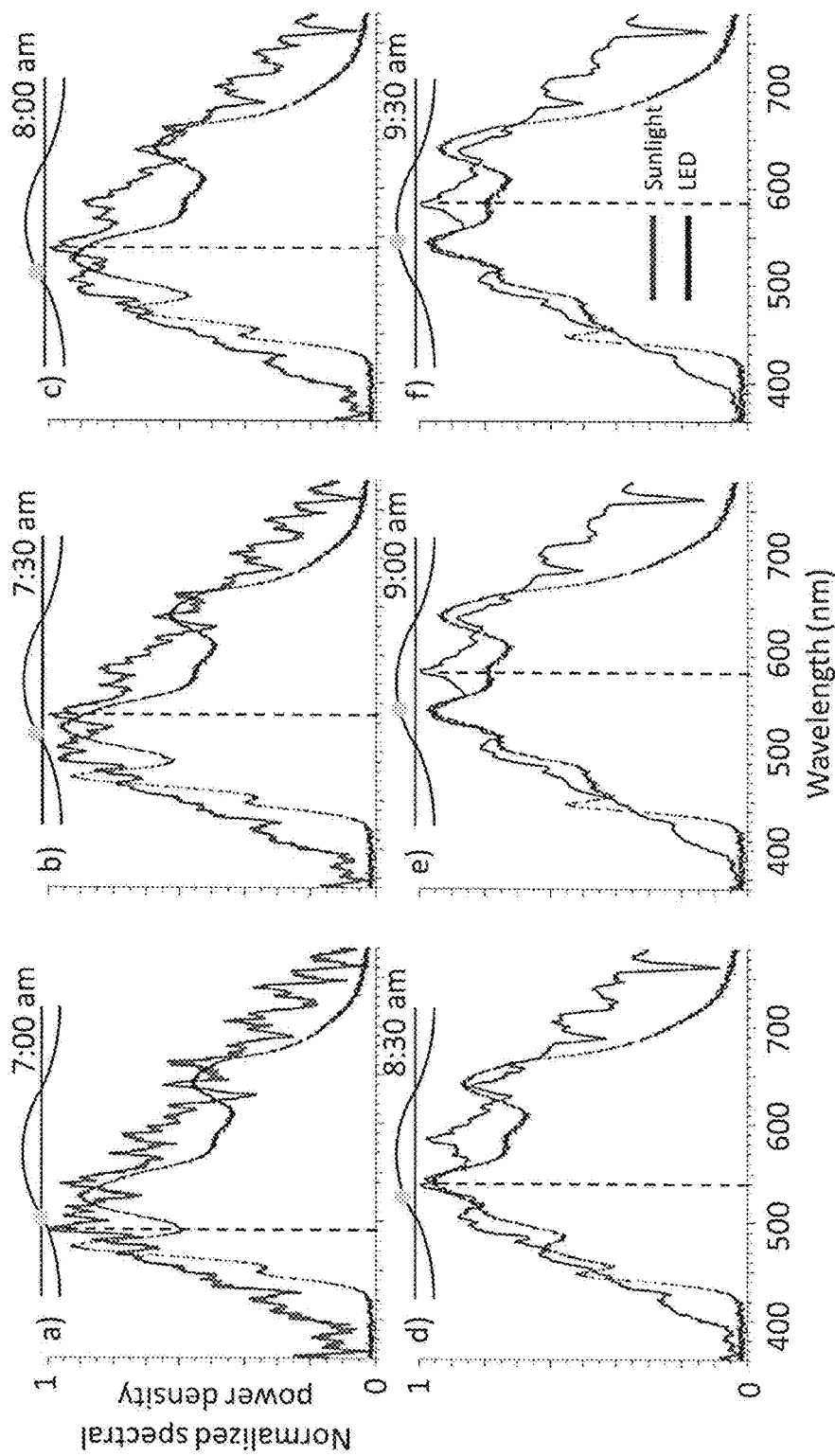
FIG. 12. Solar and LED spectra. The normalized spectral power distribution of daylight during the morning period on Jan. 25, 2016 is shown in red and the results of fitting the 4-channel LED module are shown in black. The inset graphs show the position of the sun relative to the horizon (horizontal line). The dashed vertical line indicates the position of the peak in the solar daylight illuminance spectrum. Solar daylight data were collected on Jan. 25, 2016 in Providence, R.I., USA (41.8240° N, 71.4128° W) with sun rise at 07:05 and sunset at 16:51.

FIG. 12 shows Solar and LED spectra wherein the normalized spectral power distribution of daylight during the morning period on Jan. 25, 2016 is shown in red and device-synthesized light prescriptions, made by fitting the 4-channel LED module are shown in black. A schematic inset above each frame shows the position of the sun relative to the horizon (horizontal line) at the time the sample was measured or delivered. The dashed vertical line indicates the position of the peak in the solar daylight illuminance spectrum. The Solar daylight data were collected on Jan. 25, 2016 in Providence, R.I., USA (41.8240° N, 71.4128° W) with sunrise at 07:05 and sunset at 16:51.

Figure 13:
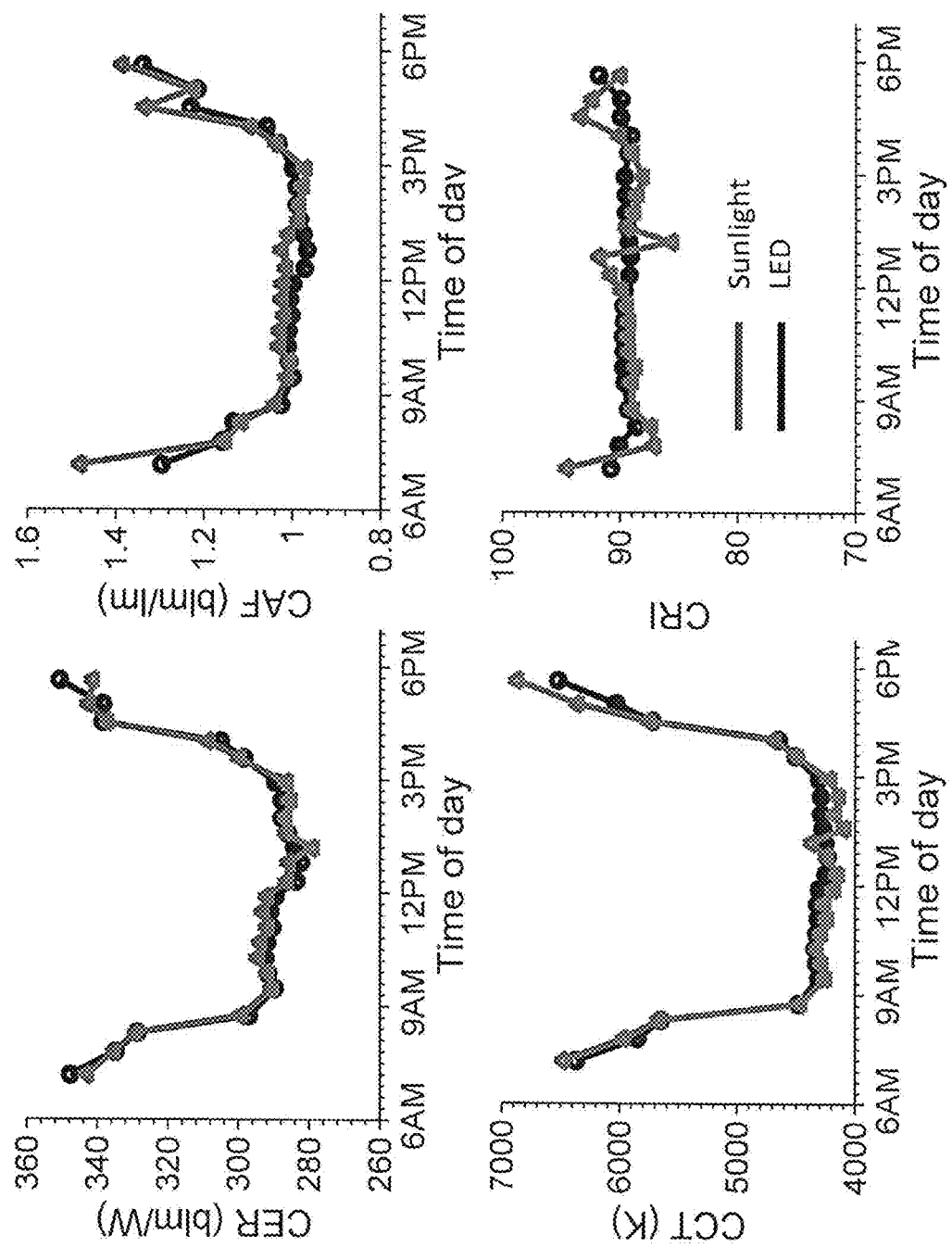
FIG. 13. Figures of merit for solar daylight and LED light, showing (a) Circadian efficacy of radiation (CER), (b) circadian action factor (CAF), (c) correlated color temperature (CCT), and (d) color rendering index (CRI). Solar data are shown in red and LED data in black. Solar data were collected on Jan. 25, 2016 in Providence, R.I., USA (41.82400 N, 71.4128° W) with sunrise at 07:05 and sunset at 16:51.
Figures 14A, 14B:
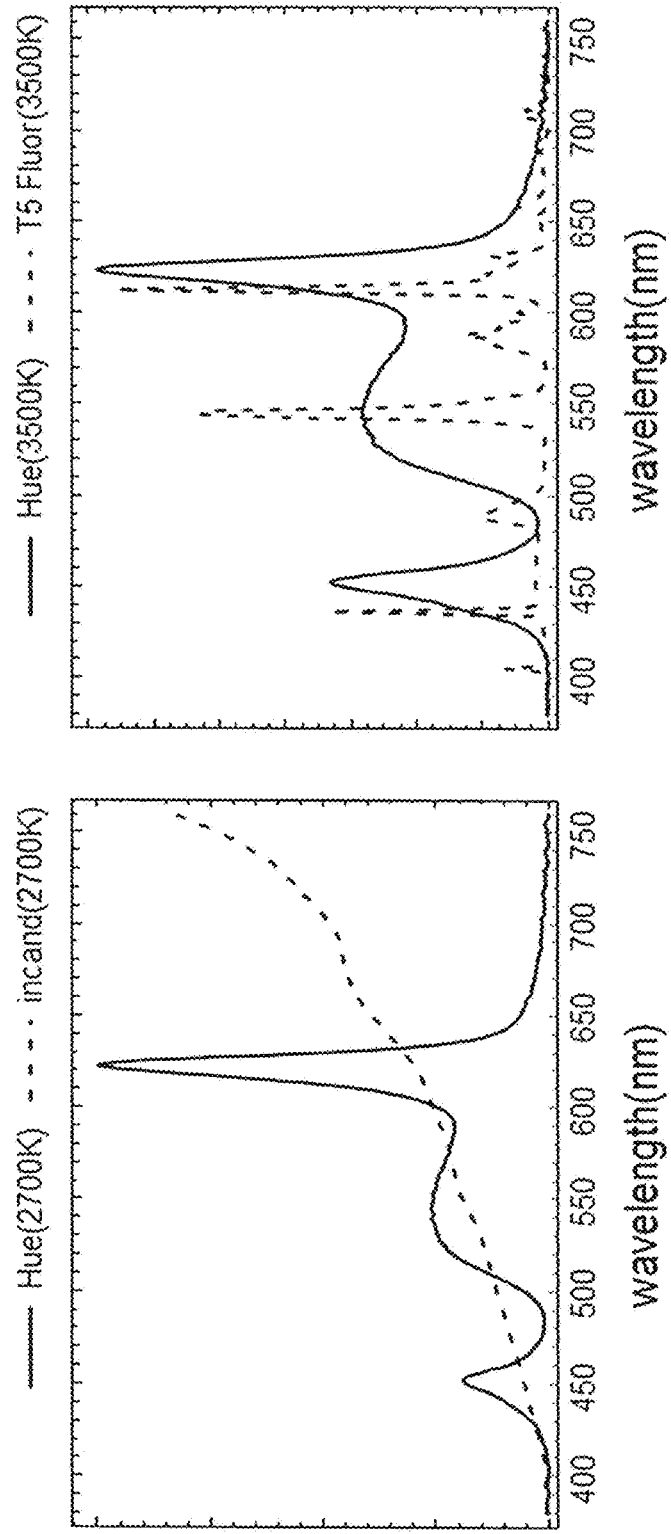
FIG. 14A illustrates spectral power distribution achieved with a Hue light set to 2700K compared to an incandescent source.
FIG. 14B shows a spectral distribution achieved with a Hue light that additionally stimulates a fluorescent source which provides a broader spectral output.
Figure 15:
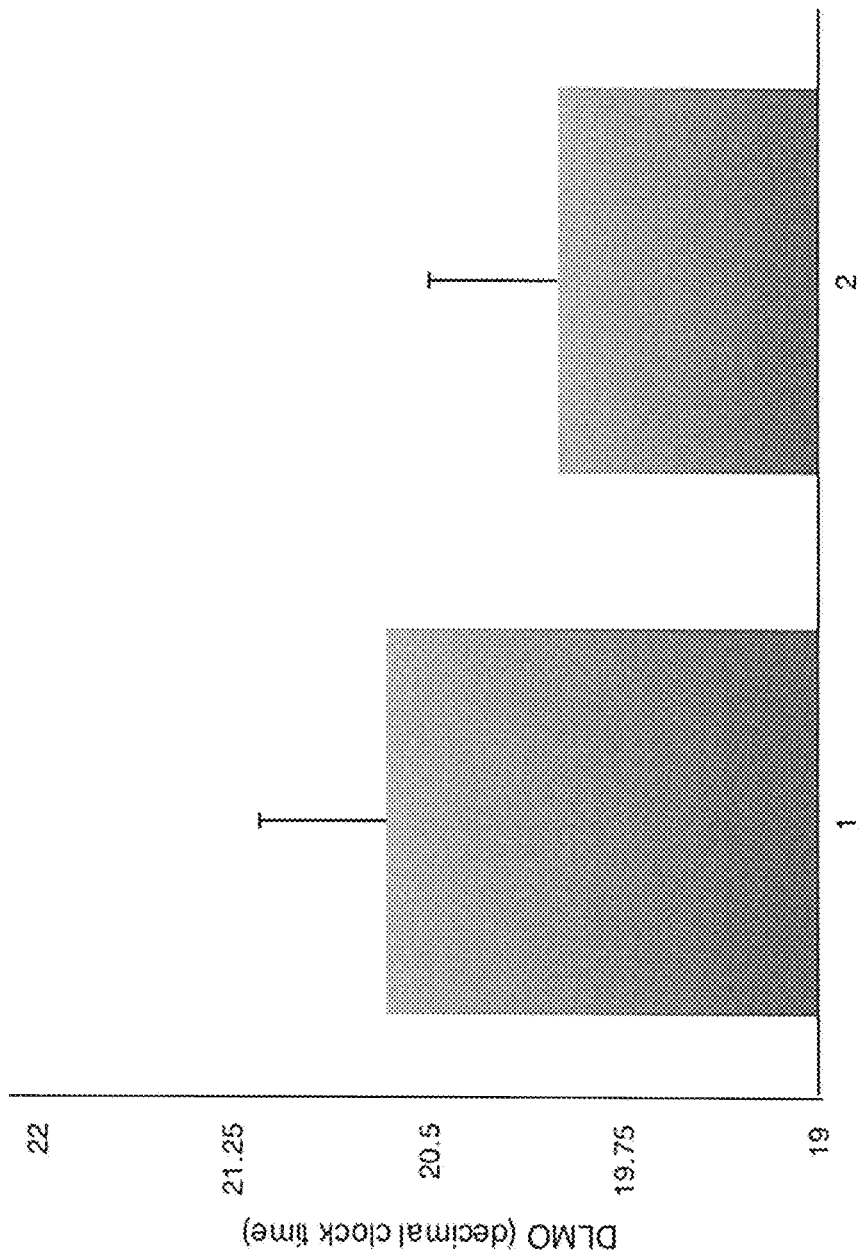
FIG. 15 shows the effect on DLMO achieved with one light recipe (decimal clock time).
Figure 16:
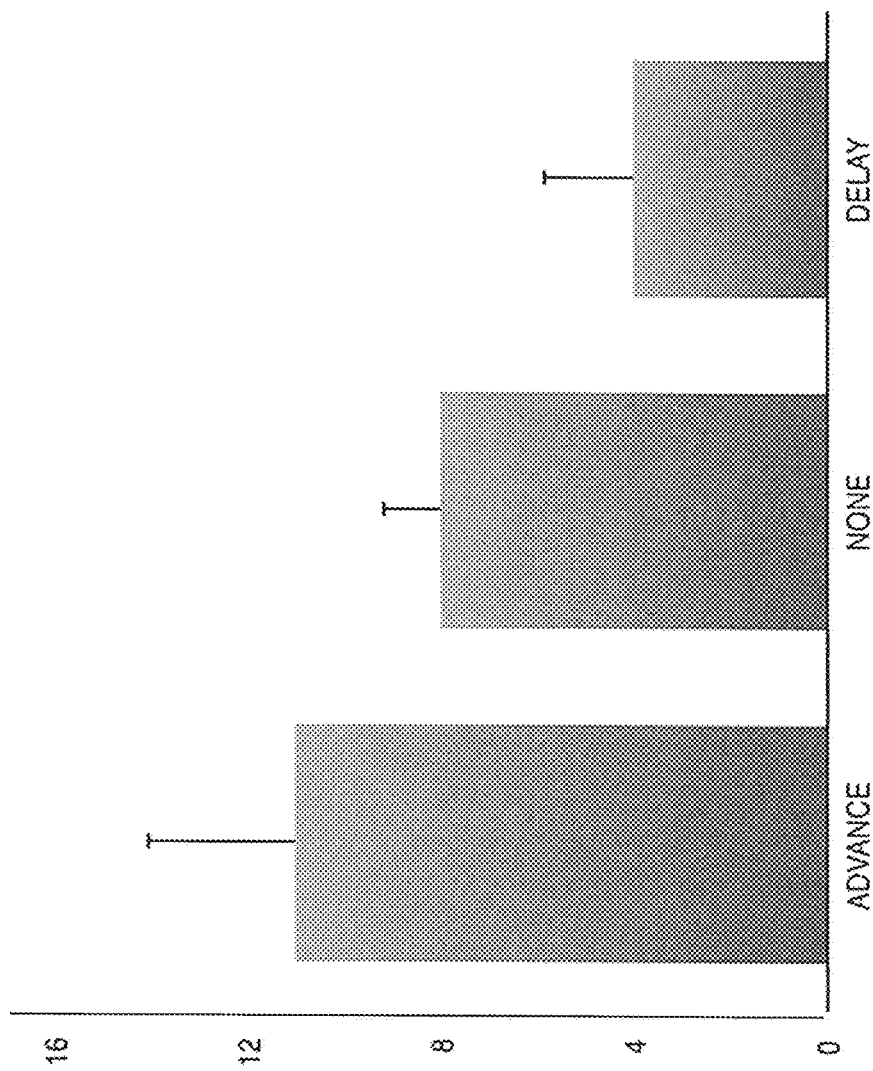
FIG. 16 shows shifts in circadian phase of students exposed to different regimens of circadian-enhanced morning light across five consecutive mornings.

FIG. 13 illustrates figures of merit for solar daylight and LED light. (a) Circadian efficacy of radiation (CER), (b) circadian action factor (CAF), (c) correlated color temperature (CCT), and (d) color rendering index (CRI). Solar data were collected on Jan. 25, 2016 in Providence, R.I., USA (41.8240° N, 71.4128° W) with sun rise at 07:05 and sunset at 16:51. Solar data are shown in red and LED data in black, indicating a very accurate artificial synthesis of the natural light spectral and intensity using the four channel LED illuminator.

It will be understood that sunlight that reaches us is filtered by different thicknesses of atmosphere as the solar angle and solar distance change with daytime and season; these changes imprint a rhythmicity to daylight, which manifests in the dim, deep blue sky during the 'Blue Hour', when the sun is below the horizon just before sunrise and just after sunset, the orange glow 'Golden Hour' when the sun is only a few degrees above the horizon, and the white appearance of noon daylight. Thus we refer to this time-of-day change in spectral power from solar angle and distance as a spectral-temporal relationship. This rhythmicity in spectral composition and intensity could also act as sources stimuli to the circadian system that consists of the sleep-awake cycle as well as the less apparent ones such as digestion. The user-based sensors of systems herein may help identify such as-yet undiscovered connections.

Circadian Phase Response Curves (PRC's) have been established as a model to show the effects of a stimulus on shifting the circadian rhythms endogenous phase (time). Light exposure often takes an intensity, duration and time of day measure to either phase advance or delay the endogenous clock, and this model is helpful in understanding that the amplitude of the endogenous response is a combination of exogenic stimulus factors as well as the internal time-of-cycle of the endogenous clock to which it is applied. Exogenous time-of-day is independent of endogenous time-of-cycle, although photoentrainment can keep them synchronized. Currently few if any PRC models have attempted to incorporate the spectral content or change in spectral content of light into account. However with the rediscovery of intrinsic photosensitive Retinal Ganglion Cells (ipRGC) in the eye, provides growing, albeit still indirect, evidence that a spectral-temporal sensitivity to light may also affect this response and should be incorporated in the modeling and control engine of the present system.

A percentage of the intrinsically photosensitive retinal ganglion cells (ipRGC) contain the photopigment melanopsin. In the context of the circadian system, these cells are sensitive to light and some experiments show most sensitive to blue light at around 460-480 nm. Photoic information is transmitted to the suprachiasmatic nucleus (SCN) of the anterior hypothalamus via the retinohypothalamic tract. The SCN is considered to be the master circadian clock in mammals. The SCN regulates melatonin release from the pineal gland. Melatonin is a hormone that is used as a circadian phase marker. More recent studies suggest that the ipRGCs as well as other photorecpeters in the eye (rods and cones for example) work together to integrate photic information that is received by the circadian system. In light of these studies it is clear that while the circadian system may be sensitive to blue light, the circadian system is responsive to a broad range of spectral distributions. Light history/photoperiod are also important factors in how the circadian system reacts to administration of light, and may be incorporated, or the sensor outputs processed to determine a lighting regimen/distribution to be provided.

Systems of the invention may integrate the various wearable and fixed sensor components to communicate with each other and with the controller, which in some embodiments contains a database to log the sensed values and preferably also a modeling engine to run algorithms that compute ideal settings for driving the light fixture channels to achieve a specified operation for stabilizing, shifting or supplementing the light levels provided to the user/subject.

Parameters included in the user model, current actual values of which are determined by the fixed and wearable sensors and are stored in the database, include sleep and wake history, activity history, circadian light dosage, environment, and biometric information.

In operation, set points may be calculated by the system algorithm which combines the user model with measured data from sensors and from optimal values derived from data to calculate the light CER and intensity set points.

Systems may be built with wireless communication between one or more of the subsystems described above, so that relevant data (such as overcast weather, time of sunrise or other data is provided by subsystems outside of or totally independent of the sensors and controls described above.

Experimentation has determined optimal times for delivering circadian or photopic lighting to act on the subject circadian state. One fairly direct application of this knowledge would be, for example to establish elementary school lighting parameters that provide blue-enhanced illumination at the start of the day, initiating a level of alertness so that all pupils are in an optimal state for focusing attention and learning. This is expected to remediate any effects that a class might otherwise suffer from fatigued students whom had stayed up too late and become fidgety, de-focused or simply prematurely drowsy/sleepy. Application of morning blue light illumination can also be applied at a time in the circadian phase that effectively advances DMLO to promote alertness and enhanced performance during the school day and facilitates sleep earlier in the evening at home The invention having been fully described and enabled by examples herein, it is further exemplified by the following claims, which are not to be construed as further limiting.

What is claimed is:

1. A system for tuning, control or remediation of a biological light-responsive state, the system comprising a light controller to control an illumination source and a sensing feedback system connected to or communicating with the controller, the controller being operative to set at least one of: spectral distribution, light intensity, light directionality, light periodicity, and a bioactive spectral band, during a programmed or specified time, providing a lighting prescription to supplement ambient or other illumination experienced by a subject in a manner effective to shift or to entrain a circadian response of the subject and thereby improve the subject's performance under changing, disrupted, unnatural extended, geographically discontinuous or spectrally deficient or inappropriate lighting, applying an illumination recipe that compensates for deficiency, or shifts or enhances the circadian response in a subject, wherein circadian phase is determined from one or more actigraphy sensors or from a sensor that detects DLMO (dim light melatonin onset) in a sample of body fluid.

2. The system according to claim 1, wherein the controller applies a Table of Prescriptive Settings for controlling light to synchronize a subject's timing or level of production of melatonin or other circadian effector so as to optimize at least one of alertness, cognition, physical performance, sleepiness, sleep, and restedness in accordance with a pre-determined scheduled event, group activity or mission event.

3. The system according to claim 1, wherein the controller provides automated control or wireless management of illumination parameters.

4. The system according to claim 3, wherein the automated control is manually adjustable by the subject or other user.

5. The system according to claim 3, wherein the automated control is not adjustable.

6. The system of claim 3 wherein at least one of timing, intensity and spectral distribution of illumination is applied to shift, or to stabilize Circadian phase.

7. The system of claim 3 which applies blue-boosted illumination for a specified time to achieve a defined Circadian phase delay.

8. The system of claim 3 which applies blue-boosted white light for several hours substantially after DLMO to achieve a Circadian phase advance; or applies a lesser intensity and duration of blue-boosted white light to achieve a phase delay over the course of one day.

9. The system according to claim 1, wherein the controller applies a palliative spectral recipe to manage or reduce fatigue or tension, a medical condition such as elevated blood pressure or a psychological condition, or a mood.

10. The system according to claim 1, wherein the controller controls at least one light source, but ideally two or more light sources to apply a prescribed illumination supplement timed to synchronize or phase-shift the subject's circadian state.

11. The system according to claim 1, wherein the controller receives a biofeedback signal indicative of a subject's circadian response or estimated circadian response and adjusts lighting control in accordance therewith to shift or strengthen circadian phase in support of an intended task, location or activity to be performed by the subject, wherein the subject has at least one scheduled performance such as; an athletic event or team activity; a military activity such as an army or air force mission or a naval pilot orders; a medical activity such as emergency room, surgical or obstetrical activity; an artistic activity such as a theater or concert performance; or a transportation endurance activity such as long distance trucking orj et plane travel.

12. The system according to claim 11, wherein the system is located in or conveniently movable to a designated remediation area of a structure selected from: an athletic facility, a police station, a fire station, an airport hangar, a compartment or a cabin of a truck, airplane, ship, an EMT vehicle, a bus, and a room in a hospital such as an intern's lounge or an operating room, nursing home, or an assisted living facility, and a school classroom.

13. The system according to claim 1 wherein the controller controls a blue-boosted LED light source and is in a kit in a container which is portable and further comprises instructions for installation and de-installation.

14. The system according to claim 1 including a sensor subsystem which is worn by or attached to the subject.

15. The system according to claim 14, which is eyewear, a headband, a hat, a cap, or a headset.

16. The system according to claim 14, wherein the sensor detects light experienced by the user, or a physiologic state of the user, or melatonin level in a body fluid of the user, or sleep/wake activity patterns, or other markers (hormones, secretions) indicative of circadian state or used to estimate circadian state.

17. The system according to claim 1, wherein the light is at least one LED.

18. The system according to claim 1, wherein the light directionality is direct light.

19. The system according to claim 1, wherein the light directionality is diffuse.

20. The system according to claim 1, wherein circadian phase is determined from one or more actigraphy sensors.

21. The system of claim 1, comprising an LED with blue light to provide high CER illumination.

22. The system of claim 21 further including an incandescent light element.

23. A method of treatment to shift or entrain circadian rhythm in a subject to reduce stress or tension prior to surgery or chemotherapy, the method comprising tuning a subject's circadian rhythms by applying the system according to claim 1 to deliver a light prescription dose effective to delay, advance, or entrain the subject's circadian phase.

24. The method according to claim 23, wherein is the dose is at least two hours, four hours, or eight hours of treatment for at least one treatment, applied prior to the surgery or chemotherapy.

* * * * *